United States Patent [19]

Hall et al.

[11] 4,395,417

[45] Jul. 26, 1983

[54] ANTIHYPERLIPIDEMIC COMPOSITIONS

[75] Inventors: Iris Hall; George Cocolas, both of Chapel Hill; James M. Chapman, Jr., Ashville, all of N.C.

[73] Assignee: Research Corporation, New York, N.Y.

[21] Appl. No.: 142,678

[22] Filed: Apr. 22, 1980

[51] Int. Cl.$^3$ .................. A61K 31/045; A61K 31/19; A61K 31/12
[52] U.S. Cl. .................. 424/270; 424/274; 424/275; 424/308; 424/309; 424/317; 424/331
[58] Field of Search ............... 548/210, 211; 424/274, 424/270, 275, 308, 309, 331, 317

[56] References Cited

U.S. PATENT DOCUMENTS

| | | | |
|---|---|---|---|
| 3,284,450 | 11/1966 | Kraaijeveld et al. | 548/210 |
| 3,607,876 | 9/1971 | Bailey et al. | 421/274 |
| 3,658,957 | 4/1972 | Roberts et al. | 424/331 |
| 3,879,468 | 4/1975 | Durden et al. | 424/331 |
| 3,940,419 | 2/1976 | Diehl et al. | 424/274 |
| 4,000,307 | 12/1976 | Nadelson | 426/274 |
| 4,116,964 | 9/1978 | Zinnes et al. | 548/210 |
| 4,213,996 | 7/1980 | Shipchandler | 424/274 |

*Primary Examiner*—Nicholas S. Rizzo
*Attorney, Agent, or Firm*—Scully, Scott, Murphy and Presser

[57] ABSTRACT

The invention concerns cyclic imides, diones, reduced diones and analogs thereof which are useful as antihyperlipidemic agents to reduce serum cholesterol and triglycerides.

14 Claims, No Drawings

ANTIHYPERLIPIDEMIC COMPOSITIONS

BACKGROUND OF THE INVENTION

This invention relates to antihyperlipidemic or hypolipidemic agents which are useful in the control of mammalian diseases associated with increased serum cholesterol or triglycerides.

SUMMARY OF THE INVENTION

It has been discovered that certain cyclic imides, diones and partially reduced diones are useful as antihyperlipidemic agents. These compounds are represented by the formulas:

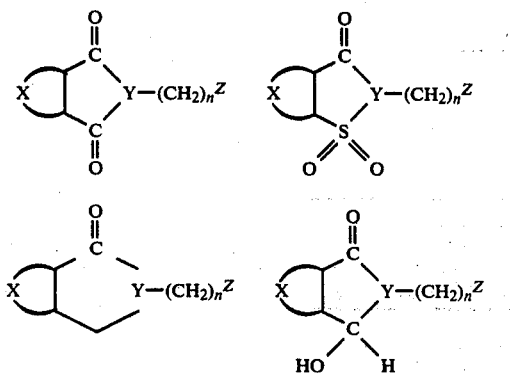

wherein X is aryl, cycloalkyl, or cycloalkylene containing up to ten carbon atoms; Y is CH or N; Z is alkyl containing up to 5 carbon atoms, carboxyl, carboalkoxyl wherein the alkyl group contains up to 4 carbon atoms, acyl containing up to 4 carbon atoms, alkylene, aryl, aralkyl or aralkylene; and n is 1 to 10. The invention includes further compounds wherein the group represented by X is replaced with at least one hydrogen on each of the carbon atoms adjacent the oxygen bearing functional groups. It includes, also, pharmaceutically acceptable acid addition salts of the compounds. Certain of the hydrogens, particularly those on aryl or cycloaliphatic rings may be substituted, for example, with a halogen atom or an alkyl group containing up to 5 carbon atoms.

Many of the compounds within the scope of this invention are known, others are novel. None have previously been utilized or suggested as hypolipidemic agents. They have been found to significantly decrease serum cholesterol, serum triglycerides and also to inhibit liver acetyl coenzyme A synthetase and carboxylase activity. Generally speaking, the best activity is found with compounds in which the value of n is from 2 to 4.

For hypolipidemic activity, the compounds were tested at 20 mg/kg/day administered I.P. to male $CF_1$ mice (~30 g). On days 9 and 16 blood was collected by tail-vein bleeding. Serum cholesterol was determined by the Liebermann-Burchard reaction. Serum triglyceride levels were determined using the Hycel commercial kits on a separate group of mice, which were bled on day 14.

Acetyl coenzyme A sythetase activity was determined by the method of Goodridge, J.Biol. Chem 248,4318. Acetyl coenzyme A carboxylase activity was determined by the method of Greenspan and Lowenstein, J.Biol. Chem. 243,6273. The ability to lower serum cholesterol with the first mentioned compound correlated with the ability to lower serum cholesterol. The ability to supress acetyl-CoA carboxylase activity positively correlated with the lowering of serum triglycerides.

The results with some representative compounds of the invention are shown in Table 1. Table 2 shows the results of the enzyme studies with the compounds of Table 1. Table 3 shows the results of similar studies with still another group of compounds.

TABLE 1

The Effects of Imide Analogs on Serum Cholesterol and Triglyceride Levels of Male Mice

| | % Control | | |
|---|---|---|---|
| | Serum Cholesterol | | Serum Triglyceride |
| Compounds ($N^a = 6$) | 9th day | 16th day | 14th day |
| 1. Phthalimide | 63 ± 13[e] | 57 ± 7[e] | 44 ± 8[e] |
| 2. 1-N—Phthalimidobutan-3-one | 67 ± 11[e] | 63 ± 7[e] | 58 ± 7[e] |
| 3. Succinimide | 78 ± 9[e] | 73 ± 12[e] | 68 ± 7[e] |
| 4. 1-N—Succinimidobutan-3-one | 90 ± 9 | 88 ± 7 | 79 ± 15 |
| 5. 1,8-Naphthalimide | 81 ± 6[e] | 61 ± 7[e] | 87 ± 12 |
| 6. 1-N—(1,8-Naphthalimido)butan-3-one | 94 ± 12 | 86 ± 9 | 54 ± 15[e] |
| 7. Saccharin | 68 ± 11[e] | 67 ± 10[e] | 51 ± 16[e] |
| 8. 1-N—(o-Benzosulfimido)butan-3-one | 60 ± 8[e] | 62 ± 6[e] | 51 ± 7[e] |
| 9. 3-N—Phthalimidopropionic Acid | 74 ± 10[e] | 55 ± 12[e] | 58 ± 9[e] |
| 10. 1-N—Phthalimidopropan-2-one | 80 ± 16 | 67 ± 12[e] | 48 ± 10[e] |
| 11. N—n-Butylphthalimide | 72 ± 11[e] | 54 ± 6[e] | 82 ± 10 |
| 1% carboxymethylcellulose (control) | 100 ± 5[b] | 100 ± 6[c] | 100 ± 6[d] |

[a] N = number of animals/group
[b] 118 mg % control value
[c] 122 mg % control value
[d] 137 mg % control value
[e] p 0.001

TABLE 2

The In Vitro Effects of Imide Analogs on Enzymes of the Cholesterol and Triglyceride Synthetic Pathways

| | % Control | | | |
|---|---|---|---|---|
| Compounds ($N^a = 6^a$) | Acetyl-CoA Synthetase | Citrate Lyase | Acetyl-CoA Carboxylase | Fatty Acid Synthetase |
| | $\bar{x} \pm$ S.D. | $\bar{x} \pm$ S.D. | $\bar{x} \pm$ S.D. | $\bar{x} \pm$ S.D. |
| 1 | 70 ± 8$^f$ | 42 ± 6$^f$ | 8 ± 4$^f$ | 105 ± 8 |
| 2 | 53 ± 12$^f$ | 34 ± 4$^f$ | 17 ± 3$^f$ | 109 ± 7 |
| 3 | 74 ± 6$^f$ | 38 ± 3$^f$ | 87 ± 7 | 98 ± 9 |
| 4 | 58 ± 6$^f$ | 38 ± 7$^f$ | 100 ± 5 | 81 ± 7$^g$ |
| 5 | 63 ± 9$^f$ | 66 ± 6$^f$ | 106 ± 6 | 86 ± 8 |
| 6 | 88 ± 5$^f$ | 60 ± 5$^f$ | 59 ± 8$^f$ | 103 ± 4 |
| 7 | 61 ± 7$^f$ | 65 ± 6$^f$ | 9 ± 2$^f$ | 93 ± 5 |
| 8 | 74 ± 9$^f$ | 47 ± 8$^f$ | 12 ± 3$^f$ | 104 ± 7 |
| 9 | 57 ± 10$^f$ | 87 ± 6$^g$ | 18 ± 4$^f$ | 107 ± 7 |
| 10 | 58 ± 7$^f$ | 76 ± 4$^f$ | 24 ± 4$^f$ | 91 ± 9 |
| 11 | 44 ± 11$^f$ | 72 ± 9$^f$ | 76 ± 3$^f$ | 75 ± 10$^g$ |
| 1% carboxymethylcellulose | 100 ± 5$^b$ | 100 ± 4$^c$ | 100 ± 7$^d$ | 100 ± 7$^e$ |

$^a$N = number of animals per group
$^b$28.5 mg acetyl CoA formed/gm wet tissue/30 min.
$^c$30.5 mg of citrate hydrolyzed/gm wet tissue/30 min.
$^d$32,010 dpm/gm wet tissue/30 min.

TABLE 3

Effects of Phthalimide Analogs on Serum Lipids in Mice$^a$ (N = 6)

| | | % Control | | | in vitro | |
|---|---|---|---|---|---|---|
| | | serum cholesterol | | serum tri- | AcCoA | lit. |
| No. | Compound | 9th day | 16th day | glycerides | synthetase | ref. |
| 1 | potassium phthalimide | 63 ± 6$^e$ | 78 ± 3$^d$ | 88 ± 4$^d$ | 78 ± 6$^e$ | |
| 2 | N—methylphthalimide | 74 ± 4$^e$ | 74 ± 8$^d$ | 68 ± 8$^e$ | 66 ± 12$^e$ | 1 |
| 3 | N—ethylphthalimide | 83 ± 4$^e$ | 76 ± 2$^e$ | 87 ± 5$^d$ | 82 ± 5$^e$ | 1 |
| 4 | N—n-propylphthalimide | 96 ± 4 | 74 ± 5 | 81 ± 9$^d$ | 67 ± 3$^e$ | 2 |
| 5 | N—n-butylphthalimide | 72 ± 10$^e$ | 54 ± 6$^e$ | 82 ± 16 | 82 ± 7$^d$ | 3 |
| 6 | N—n-pentylphthalimide | 76 ± 5$^e$ | 58 ± 3$^e$ | 75 ± 16$^c$ | 68 ± 6$^e$ | 4 |
| 7 | N—n-hexylphthalimide | 96 ± 5 | 66 ± 4$^e$ | 84 ± 8$^d$ | 71 ± 12 | 3 |
| 8 | N—n-heptylphthalimide | 99 ± 7 | 72 ± 4$^e$ | 84 ± 6$^d$ | 71 ± 5$^e$ | 5 |
| 9 | N—n-octylphthalimide | 101 ± 7 | 82 ± 3$^d$ | 77 ± 4$^e$ | 76 ± 7$^e$ | 6 |
| 10 | 1-N—phthalimidopropan-2-one | 80 ± 16$^b$ | 67 ± 12$^e$ | 48 ± 10$^e$ | 58 ± 7$^e$ | 7 |
| 11 | 1-N—phthalimidobutan-3-one | 67 ± 11$^e$ | 63 ± 7$^e$ | 58 ± 7$^e$ | 53 ± 12$^e$ | 8 |
| 12 | 1-N—phthalimidopentan-4-one | 71 ± 6$^e$ | 63 ± 5$^e$ | 59 ± 13$^e$ | 62 ± 3$^e$ | 9 |
| 13 | 1-N—phthalimidohexan-5-one | 65 ± 9$^e$ | 65 ± 7$^e$ | 77 ± 5$^e$ | 68 ± 6$^e$ | 10 |
| 14 | 1-N—phthalimidoheptan-6-one | 71 ± 6$^e$ | 75 ± 12$^c$ | 88 ± 5$^d$ | 85 ± 3$^e$ | 11 |
| 15 | 2-N—phthalimidoacetic acid | 76 ± 7$^e$ | 68 ± 7$^e$ | 72 ± 9 | 72 ± 12$^e$ | 12 |
| 16 | 3-N—phthalimidopropionic acid | 74 ± 7$^e$ | 55 ± 11$^e$ | 58 ± 10$^e$ | 57 ± 7$^e$ | 13 |
| 17 | 4-N—phthalimidobutyric acid | 80 ± 7$^e$ | 68 ± 6$^e$ | 59 ± 14$^e$ | 64 ± 12$^e$ | 14 |
| 18 | 5-N—phthalimidovaleric | 83 ± 9$^d$ | 77 ± 4$^d$ | 54 ± 5$^e$ | 76 ± 8$^e$ | 15 |
| 19 | 6-N—phthalimidocaproic acid | 81 ± 6$^e$ | 67 ± 3$^e$ | 51 ± 12$^e$ | 59 ± 9$^e$ | 16 |
| 20 | N—phthalimidomethyl acetate | 61 ± 9$^e$ | 62 ± 4$^e$ | 57 ± 25$^e$ | 62 ± 10$^e$ | 17 |
| 21 | N—phthalimidoethyl acetate | 93 ± 13 | 95 ± 1$^e$ | 82 ± 7$^d$ | 81 ± 6$^e$ | 18 |
| 22 | N—phthalimidopropan-1-ol acetate | 102 ± 4 | 66 ± 2$^e$ | 89 ± 9 | 84 ± 2$^h$ | |
| 23 | N—phthalimidobutan-1-ol acetate | 93 ± 9 | 66 ± 5$^e$ | 88 ± 7$^b$ | 83 ± 2$^e$ | 19 |
| 24 | 1% carboxymethylcellulose$^j$ | 100 ± 2$^f$ | 100 ± 11$^g$ | 100 ± 6$^h$ | 100 ± 6$^i$ | |

$^a$N = number of mice per test group = 6.
$^b$p = 0.25.
$^c$p = 0.10.
$^d$p = 0.005.
$^e$p = 0.001.
$^f$115 mg %.
$^g$118 mg %.
$^h$138 mg %.
$^i$10.8 mg/g wet tissue.
$^j$Control.

In Table 3 literature references are given as illustrative of the general procedures by which compounds of the invention are prepared. The references are as follows:

1. Sakellarios, Helv. Chim. Acta 29, 1675 (1946)
2. Shoslakovskii et al, Bull Acad. Sci. USSR, Div. Chem. Sci., 455(1954)
3. Sterk et al, Arzneim-Forsch., 18, 798 (1968)
4. Meisenheimer et al, Justus Liebigs, Ann. Chem., 479, 211(1930)
5. Vanags, Acta Univ. Latv., Kim, Fak. Serv., 4(8), 405(1939)
6. Salzberg, U.S. Pat. No. 2,101,323
7. Lanchaster et al, J. Org. Chem., 23, 1208(1958)
8. Abdel-Monen et al, J. Med. Chem., 17, 447(1974)
9. Baker et al, U.S. Pat. No. 2,625,549
10. Gabriel, Chem. Ber., 42, 1249(1909)
11. Billman et al, J. Am. Chem. Soc., 70, 1473(1948)
12. Chodroff et al, J. Am. Chem. Soc., 69, 256(1947)
13. Balenovic et al, J. Org. Chem. 19, 1591(1954)
14. Fujii et al, J. Med. Chem., 14, 354(1971)

15. Taub, U.S. Pat. No. 3,210,313
16. Nefhens et al, Recl. Trav. Chim. Pays-Bas, 82, 941(1963)
17. Rowland, U.S. Pat. No. 2,547,542

The disclosure of all of these publications are incorporated herein by reference.

The compounds used in the invention are not only highly active. They also are non-toxic. The $LD_{50}$ of 1-N-phthalamidopropan-2-one, for example, is higher than 2 g/kg in mice since no deaths were observed at this concentration. Moreover, there is no evidence that the weight of any of the major organs is altered as a result of treatment with compounds used in the invention.

Unlike many hypolipidemic agents, the compounds used in the invention do not manifest estrogenic activities. For example, with 1-N-phthalamidopropan-2-one, there was, in mice, no decrease in the size of the vas deferens, vesicular or testes after a 16 day treatment at 10 (mg/kg)/day, nor did the drug demonstrate uterotropic effects in ovariectomized immature females at 20 mg/kg. The compound caused no hypertophy of the adrenal, a characteristic of many previously known hypercholesteremic agents.

When the compounds used in this invention are employed as hypolipidemic agents, they may be administered to warm-blooded mammals, e.g. mice, rats, rabbits, dogs, cats, monkeys, etc. alone or in combination with pharmacologically acceptable carriers, the proportion of which is determined by the solubility and chemical nature of the compounds, chosen route of administration and standard biological practice. For example, they may be administered orally in the form of tablets, capsules, lozenges, and the like containing such excipients as starch, milk sugar, and so forth. They may also be administered orally in the form of solutions or they may be injected parenterally. For parenteral administration they may be used in the form of sterile solution containing other solutes, for example, enough saline or glucose to make the solution isotonic.

The dosage of the agents will vary with the form of administration and the particular compound chosen. Furthermore, it will vary with the particular subject under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in the range of from about 10 mg to about 250 mg per kilo per day, although as mentioned above, variations will occur.

Typical compounds within the scope of this invention include: phthalimide; N-butylphthalimide; 1-N-phthalimidobutan-3-one; 3-N-phthalimidopropionic acid; N-phthalimidomethyl acetate; 1,8-naphthalimide; N-butyl-1-8-naphthalimide; 1-N-(1',8'-naphthalimido)butan-3-one; 3-N-(1',8'-naphthalimido)propionic acid; N-1,8-naphthalimidomethyl acetate; indan-1,3-dione; 2-butylindan-1,3-dione; 1-(1',3'-diketo-2'-indanyl)butan-3-one; 3-(1',3'-diketo-2'-indanyl)propionic acid; 1,3-diketo-2-indanylmethyl acatate; saccharin; (o-benzosulfinimide); N-butylsaccharin;(N-butyl-o-benzosulfinimide); 1-N-o-benzosulfinimidobutan-3-one; 3 N-o-benzosulfinimidopropionic acid; N-o-benzosulfinimidomethyl acetate; hydroxyphthalamidine; N-butylhydroxyphthalamidine; 1-N-hydroxyphthalamidinebutan-3-one; 3-N-hydroxyphthalamidinopropionic acid; N-hydroxyphthalamidinomethyl acetate; phthalamidine; N-butylphthalamidine; 1-N-phthalamidinobutan-3-one; 3-N-phthalamidinopropionic acid; N-phthalamidinomethyl acetate; 1-oxohydrindine; 2-butyl-1-oxohydrindine; 1-(1'oxo-2'-hydrindinyl)-butan-3-one; 3-(1'oxo-2'-hydrindinyl)propionic acid; 1-oxo-2-hydrindinylmethyl acetate; succinimide; N-butylsuccinimide; 1-N-succinimidobutan-3-one; 3-N-succinimidopropionic acid; N-succinimidomethyl acetate; 1,2-naphthalimide; N-hexyl-1,2-naphthalimide; 1-N-(1',2'-naphthalamido)heptanoic acid; N-1',2'-naphthalamidomethylacetate; 2,3-naphthalimide; N-hexyl-2,3-naphthalimide; 1-N-(2',3'-naphthalamido)pentane-3-one; 3-N-(2',3'-naphthalamido)hepanoic acid; N-2',3'-naphthalamidomethyl acetate; 2-3-naphthosulfinimide; N-nonyl-2,3-naphthosulfinimide; 1-N-(2',3'-naphthosulfinimido)hexane-2-one; 4-N-(2',3'-naphthosulfinimido)-butanoic acid; N-2',3'-naphthosulfinimidohexyl butyrate; 1,8-naphthosulfinimide; N-nonyl-1,8-naphthosulfinimide; 1-N-(1'8'-naphthosulfinimido)hexane-2-one; 4-N-(1',8'-naphthosulfinimido)butanoic acid; N-1',8'-naphthosulfinimidohexyl butyrate.

As indicated above, compounds of the classes illustrated by the general formulas are known, although not known for the valuable pharmacalogical activity disclosed herein. Accordingly general procedures for their preparation are known. Literature references to some of the procedures are identified above. It may be helpful however for a better understanding of the invention to briefly review some of the synthetic methods.

One procedure which is generally applicable, once the closed ring system has been synthesized, is the Gabriel reaction in which an alkali metal salt of the heterocyclic compound is reacted with an appropriate alkyl halide. This reaction is generally applicable because a hydrogen attached to a nitrogen or carbon adjacent a carbonyl group is acidic and easily replaced by an alkali metal such as sodium or potassium. This initial replacement normally takes place in alcoholic solution or suspension by reaction of the basic compound with a sodium or potassium alkoxide. The salt may be isolated, but it is not necessary to do so.

The salt is reacted in a reaction inert organic solvent with at least an equimolar quantity of the selected halide. Typically, the reaction takes place at a temperature of from 70° C. to 150° C. during a period of from 3 to 10 hours.

The product may be isolated by any convenient procedure. It may be isolated for example, by evaporation of the solvent and under vacuum, extraction of the residue with ahalogenated hydrocarbon or other volatile solvent which is then suitably washed with aqueous alkali and water, dried and evaporated to provide the desired product.

Alkyl halides, haloketones, haloesters, haloacids and haloalcohols which can be employed in the synthesis are available commercially or can by synthesized by procedures well known in the art. For the production of acids, it is preferred to carry out the original reaction with a halocarbalkoxy ester and then form the acid by hydrolytic removal of the alkoxy group by treatment with aqueous acid or alkali.

N-carboxylic acid substituted compounds can also be prepared by reaction of the appropriate amino acid with an anhydride followed by ring closure by dehydration.

Y-substituted 3-butanones can be prepared by reaction of the appropriate substrate with methyl vinyl ketone in an alkaline media under the so-called Michael conditions.

Several additional synthetic procedures for placing the Y-substituents are illustrated in the examples.

Compounds with one or two keto groups, for example, hydroxypthalamidine, pthalamidine, 1-oxyhydrimidine and the like can be made by known series of reactions.

Anthranilic acid, for example, can be converted to a 1-substituted compound of the invention by the following series of reactions:
1: Form o-cyanobenzoic acid by diazotization in the presence of potassium cyanide and a cuprous salt.
2: Form the corresponding aminomethylene compound by reduction with hydrogen under acidic conditions in the presence of a noble metal catalyst such as palladium on carbon.
3: React resulting compound with an RX compound where X is halogen and R is the Y-substituent.
4: Ring close in the presence of acid to produce a Y-substituted 1-oxyhydrimidine.

An alternative procedure utilizes benzyl malonic ester, for example the diethyl ester as a starting compound followed by:
1: Replacement of the alpha hydrogen by reaction with an RX compound where X is halogen and R is the Y-substituent.
2: Simultaneous hydrolysis and decarboxylation to produce an alpha or beta phenylpropionic acid.
3: Convert to the acid chloride.
4: Ring closure under Friedel-Crafts conditions.

Y-substituted hydroxyphthalamidines and the analogous carbon compounds can be produced by selective reduction of the corresponding diket compounds, for example with potassium borohydride.

The acids and bases which can be used to prepare the pharmacologically acceptable acid addition and basic salts of this invention are those containing non-toxic anions and cations. They include, for example, sodium, potassium and ammonium hydroxide, carbonate, bicarbonate and acetates; as well as hydrochloric, sulfuric, phosphoric, acetic, lactic, citric, tartaric, oxalic, succinic, maleic, gluconic, saccharic and like acids. The salts are prepared by known procedures.

The following examples are given by way of illustration only and are not to be considered limitations of this invention many apparent variations of which can be made without departing from its spirit or scope.

EXAMPLE 1

SYNTHESIS OF Y-ALKYL SUBSTITUTED COMPOUNDS

The synthesis of N-ethylphthalimide and n-amylphthalimide is illustrative of the general procedure by which N-alkyl and C-alkyl compounds within the scope of this invention can be prepared. Since the hydrogen to be replaced with an alkyl group is acidic it can be replaced with an alkali metal by reaction with an alkoxide such as sodium or potassium ethoxide. Those skilled in the art will recognize the conditions of the reactions as the general conditions of the Gabriel synthesis.

Method A

To 18.5 g (0.10 mol) of potassium phthalimide suspended in 100 ml of dry DMF, was added 0.11 mol of methyl-p-toluenesulfonate, ethyl iodide, or 1-bromopentane. The reaction mixture was heated to 90°–100° C. for a five to eight hour period. The volatile material was removed under reduced pressure, 150 ml of $CHCl_3$ added to the residue, and the mixture washed with 100 ml of 1 N aqueous NaOH and two 100 ml portions of $H_2O$. The $CHCl_3$ layer was dried over $Na_2SO_4$, evaporated, and the N-alkyl phthalimide purified by recrystallization or distilled in vacuo.

EXAMPLE 2

SYNTHESIS OF Y-KETONE SUBSTITUTED COMPOUNDS

The synthesis of 1-N-phthalimidobutan-3-one and 1-N-phthalimidohexan-5-one or 1-N-phthalimidoheptane-6-one under Michael conditions or through an acetoacetic ester synthesis is illustrative of general procedures for the preparation of N-alkyl alkyl hetones within the scope of the invention.

1-N-Phthalimidobutan-3-one

A solution of 44.1 g (0.30 mol) phthalimide in 200 ml of ethyl acetate, containing a catalytic amount of sodium ethoxide, was maintained at 70°–78° C., whereupon 21.7 g (0.31 mol) of methyl vinyl ketone was added over a 15 minute period. The resulting reaction mixture was refluxed an additional 1.25 hr, then allowed to cool, and neutralized with acetic acid. Removal of the ethyl acetate under reduced pressure afforded 53 g (82%) 1-N-phthalimidobutan-3-one which melted at 114°–116° C. when recrystallized from 2-propanol.

1-N-Phthalimidohexan-5-one

Ethyl acetoacetate (8.67 g, 0.067 mol) in 132 ml ethanol was allowed to react with 1.05 g (0.046 mol) of sodium. When the reaction was complete, 9.52 g (0.032 mol) of 3-bromopropylphthalimide was added and the resulting solution refluxed 23 hrs. To the resulting yellow solution was added 113 ml of 4 N HCl and the product refluxed for four additional hours then allowed to cool. The volatile material was removed under reduced pressure, 60 ml of $H_2O$ added to the residue and the resulting mixture extracted with four 140 ml portions of ethyl acetate. The ethyl acetate solution was reduced to 100 ml, dried over $MgSO_4$, and distilled in vacuo to yield 3.5 g (45% 1-N-phthalimidohexan-5-one (bp 176°–186° C., 0.05 mmHg). m.p. 65°–67° C. (ether).

1-N-phthalimidoheptan-6-one

Ethyl acetoacetate, 3.41 g (0.026 mol) in 48 ml ethanol was reacted with 0.40 g (0.01 mol) of sodium. When the reaction was complete, 4.0 g (9.914 mol) of 4-bromobutylphthalimide was added and the resulting solution refluxed 22 hrs. To the resulting yellow solution was added 40 ml of 4 N HCl and refluxing continued for 5 hrs. Upon cooling, the volatile material was removed under reduced pressure 50 ml of $H_2O$ was added to the residue, and the resulting mixture extracted with four 150 ml portions of ethyl acetate. The ethyl acetate solution was reduced to 100 ml, dried over $MgSO_4$, and distilled under high vacuum to yield 1.75 g (48%) 1-N-phthalimidoheptan-6-one (bp 166°–176° C., 0.25 mmHg). m.p. 71.5°–74° C. (ether).

EXAMPLE 3

SYNTHESIS OF CARBOXYLIC ACID SUBSTITUTED COMPOUNDS

The synthesis of 3-N-phthalimide propionic, butyric, valeric and caproic acids by reaction of the corresponding anhydride with an amino substituted carboxylic acid followed by vinyl closure illustrates one general method for preparing the carboxylic acid substituted compounds of this invention.

To 7.41 g (0.50 mol) of phthalic anhydride dissolved in 50 ml of acetone, was slowly added 0.05 mol of the appropriate amino acid, e.g. 3-aminopropionic, 4-aminobutyric, 5-aminovaleric, or 6-aminocaproic acids, in 50 ml of acetone. After the addition was complete the acetone was removed under reduced pressure to yield a white solid. The solid was suspended in 100 ml toluene and the mixture refluxed. The water formed in the reaction was collected by azeotropic distillation in a Dean Stark trap. After 0.9 ml of water had been collected, the reaction mixture was allowed to cool overnight to precipitate the phthalimido-N-alkanoic acid.

EXAMPLE 4

SYNTHESIS OF Y-CARBOALKOXY SUBSTITUTED COMPOUNDS

The synthesis of N-phthalimidopropan-1-ol acetate is illustrative of one general procedure for preparing carbalkoxy substituted compounds within the scope of the invention by first forming an alcohol following the general procedure of Example 3 followed by esterification.

3-N-Phthalimido-1-propanol was obtained by slowly adding 18.8 g (0.25 mol) of 3-amino-1-propanol to 37 g (0.25 mol) of phthalic anhydride in 200 ml of toluene. After the addition was complete, the reaction mixture was refluxed until the theoretical amount of water had been collected in a Dean Stark trap. The reaction mixture was allowed to cool, and the product precipitated (46 g, 90%).

Acetate esters of the above alcohols and N-hydroxyethyl phthalimide were obtained by acetylation with acetic anhydride and pyridine. N-Phthalimidopropan-1-ol acetate was obtained in 64% yield (m.p. 63°–65° C., MeOH). Anal. ($C_{13}H_{13}NO_4$)C,H.

EXAMPLE 5

SYNTHESIS OF Y-CARBOALKOXY SUBSTITUTED COMPOUNDS another general method of preparing esters within the scope of this invention using Gabriel conditions as further generally illustrated and described in Example 1.

A mixture of 2.54 g (0.013 mol) 4-bromobutyl acetate, and 4.8 g (0.026 mol) of potassium phthalimide was heated at 190°–200° C. for ten hours. Upon cooling, 50 ml of water was added, and the resulting mixture extracted with three 150 ml portions of ethyl acetate. The volume of the ethyl acetate layer was reduced to 100 ml, and this layer successively washed with 50 ml of 10% NaOH and 50 ml of $H_2O$. The ethyl acetate was separated and evaporated to a light yellow oil which solidified upon addition of ethanol and ice (1.5 g, 44%). m.p. 58.5°–60.5° C. (EtOH-$H_2O$).

EXAMPLE 6

INJECTABLE COMPOSITION

A sufficient amount of 3-N-(1,8-naphthalamide)propionic acid to provide a concentration of 10 mg/cc was formed into a micronized powder and suspended in a 1% carboxymethyl cellulose mixture in sterile distilled water.

EXAMPLE 7

ORAL SUSPENSION

A sufficient amount of 3-N-succinimide propionic acid was mixed with a 10% suspension of tragacanth in sterile distilled water to provide a suspension containing 5 mg/cc of active agent. The composition was mixed in a colloid mill.

EXAMPLE 8

TABLETS

A mixture containing one part N-phthalimide O-acetophenone, 4 parts lactose and 0.1 part starch was formed into a slug by compression. The slug was processed through an oscillating granulator, 0.002 parts of calcium stearate added, and the mixture formed into tablets, each tablet containing 25 mg hypolipidemic agent, 100 mg lactose, 2.5 mg starch and 0.5 mg calcium stearate.

What is claimed is:

1. Antihyperlipidemic compositions comprising a pharmaceutically acceptable carrier and, as the principal active ingredient, a compound of the group represented by the formulas:

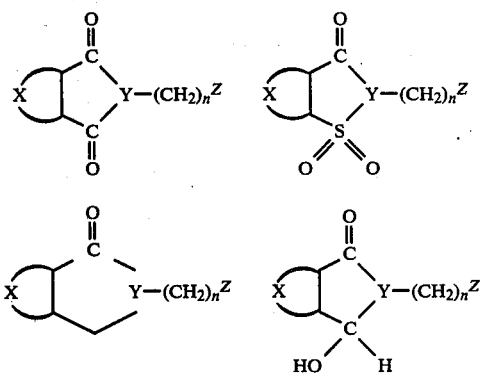

wherein X is aryl, cycloalkyl, or cycloalkylene containing up to ten carbon atoms; Y is CH or N; Z is alkyl containing up to five carbon atoms, carboxyl, carboalkoxyl wherein the alkyl group contains up to four carbon atoms, acyl containing up to four carbon atoms, alkylene, aryl, aralkyl or aralhylene; n is 1 to 10; and further compounds wherein the group represented by X is replaced with at least one hydrogen on each of the carbon atoms adjacent the oxygen bearing functional groups and pharmaceutically acceptable acid; and alkali metal addition salts thereof.

2. A composition as in claim 1 wherein the compound is 3-N-(1,8-naphthalamido)propionic acid.

3. A composition as in claim 1 wherein the compound is 3-N-succinimido propionic acid.

4. A composition as in claim 1 wherein the compound is 3-N-saccharin propionic acid.

5. A composition as in claim 1 wherein the compound is N-phthalimido o-acetophenone.

6. A composition as in claim 1 wherein the compound is 3-N-phthalimidopropionic acid.

7. A compound as in claim 1 wherein n is 2 to 4.

8. A method of controlling hyperlipidemia in mammals which comprises administering to said mammal an effective amount for controlling hyperlipidemia of a compound of the formula:

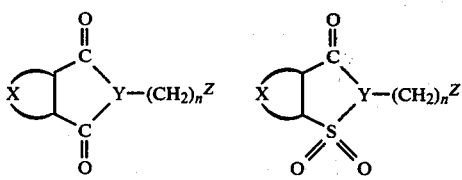

-continued wherein X is aryl, cycloalkyl, or cycloalkylene containing up to ten carbon atoms; Y is CH or N; Z is alkyl containing up to five carbon atoms, carboxyl, carboalkoxy wherein the alkyl group contains up to four carbon atoms, acyl containing up to four carbon atoms, alkylene, aryl, aralkyl or aralkylene; n is 1 to 10; and further compounds wherein the group represented by X is replaced with at least one hydrogen on each of the carbon atoms adjacent the oxygen bearing functional groups and pharmaceutically acceptable acid; and alkali metal addition salts thereof.

9. A method as in claim 8 wherein the compound is 3-N-(1,8-naphthalamido)propionic acid.

10. A method as in claim 8 wherein the compound is 3-N-succinimido propionic acid.

11. A method as in claim 8 wherein the compound is 3-N-saccharin propionic acid.

12. A method as in claim 8 wherein the compound is N-phthalimido o-acetophenone.

13. A method as in claim 8 wherein the compound is 3-N-phthalimidopropionic acid.

14. A method as in claim 8 wherein the compound is one in which n is 2 to 4.

* * * * *

UNITED STATES PATENT AND TRADEMARK OFFICE
CERTIFICATE OF CORRECTION

PATENT NO. : 4,395,417
DATED : July 26, 1983
INVENTOR(S) : Iris Hall, et al.

It is certified that error appears in the above-identified patent and that said Letters Patent are hereby corrected as shown below:

Column 9, line 51, after "SUBSTITUTED COMPOUNDS" and before "another" insert --The synthesis of N-phthalimidobutan-1-ol acetate illustrates--

Signed and Sealed this

Second Day of April 1985

[SEAL]

Attest:

DONALD J. QUIGG

Attesting Officer

Acting Commissioner of Patents and Trademarks